United States Patent
Knapp et al.

(10) Patent No.: US 8,298,329 B2
(45) Date of Patent: Oct. 30, 2012

(54) NANO-CRYSTALLINE DENTAL CERAMICS

(75) Inventors: Kenneth E. Knapp, Newport Beach, CA (US); Steven M. Maginnis, Irvine, CA (US); Wolfgang Friebauer, Costa Mesa, CA (US); Robin A. Carden, San Juan Capistrano, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 268 days.

(21) Appl. No.: 12/770,623

(22) Filed: Apr. 29, 2010

(65) Prior Publication Data

US 2011/0269618 A1 Nov. 3, 2011

(51) Int. Cl.
  *C09K 3/00* (2006.01)
  *C04B 35/48* (2006.01)
  *C04B 35/49* (2006.01)
  *A61C 13/00* (2006.01)
  *A61B 5/117* (2006.01)

(52) U.S. Cl. ........... 106/35; 501/103; 433/167; 433/229

(58) Field of Classification Search .................. 501/102, 501/103, 152; 106/35; 433/167, 171, 201.1, 433/202.1, 229
See application file for complete search history.

(56) References Cited

U.S. PATENT DOCUMENTS

| | | | |
|---|---|---|---|
| 3,432,314 A * | 3/1969 | Mazdiyasni et al. | .......... 501/103 |
| 4,520,114 A | 5/1985 | David | |
| 4,719,091 A | 1/1988 | Wusirika | |
| 4,742,030 A | 5/1988 | Masaki et al. | |
| 5,250,480 A | 10/1993 | Hoshino et al. | |
| 5,320,800 A | 6/1994 | Siegel et al. | |
| 5,460,701 A | 10/1995 | Parker et al. | |
| 5,472,749 A | 12/1995 | Dravid et al. | |
| 5,514,350 A | 5/1996 | Kear et al. | |
| 5,618,475 A | 4/1997 | Johnson et al. | |
| 5,665,277 A | 9/1997 | Johnson et al. | |
| 5,824,089 A | 10/1998 | Rieger | |
| 5,874,134 A | 2/1999 | Rao et al. | |
| 6,030,914 A | 2/2000 | Matsui | |
| 6,087,285 A | 7/2000 | Oomichi et al. | |
| 6,165,925 A | 12/2000 | Rieger | |

(Continued)

OTHER PUBLICATIONS

Casolco, S.R. et al. "Transparent/translucent polycrystalline nanostructured yttria stabilized zirconia with varying colors." Scripta Materialia 58. Nov. 14, 2007. pp. 516-519. Published by Elsevier Ltd.

(Continued)

*Primary Examiner* — Noah Wiese
(74) *Attorney, Agent, or Firm* — Mark Lauer; Silicon Edge Law Group LLP

(57) ABSTRACT

Unlike conventional dental ceramic powder made by grinding, dental ceramic nanocrystals are formed by vaporization into individual particles. Tetragonal zirconia particles thus formed are not broken into pieces, and so do not transform to weaker monoclinic zirconia and weaker sintered products. The particles created by this approach can be much smaller, and dental prostheses sintered from this powder can be stronger and more realistic. For instance, the smaller size of sintered tetragonal zirconia crystals increases optical translucence by reducing scattering from birefringence, and the small average particle size and tight distribution of sizes and shapes can essentially eliminate pores in a sintered product. Cylindrical and spherical particles can be manufactured by this approach, whereas prior art dental ceramic particles were generally neither. In addition to tetragonal zirconia, various dental ceramic particles and powders can be made by this approach, which can be used to form various sintered dental prostheses.

11 Claims, 9 Drawing Sheets

U.S. PATENT DOCUMENTS

| | | |
|---|---|---|
| 6,376,590 B2 | 4/2002 | Kolb et al. |
| 6,508,855 B2 | 1/2003 | Gardner et al. |
| 6,713,421 B1 | 3/2004 | Hauptmann et al. |
| 6,982,073 B2 | 1/2006 | Sabacky et al. |
| 7,012,214 B2 | 3/2006 | Schroder et al. |
| 7,241,437 B2 | 7/2007 | Davidson et al. |
| 7,429,422 B2 | 9/2008 | Davidson et al. |
| 7,538,055 B2 | 5/2009 | Tsukuma et al. |
| 7,547,431 B2 | 6/2009 | Yadav et al. |
| 7,553,789 B2 | 6/2009 | Fujisaki |
| 7,575,711 B2 | 8/2009 | Johnson, Jr. |
| 7,601,403 B2 | 10/2009 | Anseimi-Tamburini et al. |
| 7,608,552 B2 | 10/2009 | Meyer et al. |
| 7,622,098 B2 | 11/2009 | Taube et al. |
| 7,655,586 B1 * | 2/2010 | Brodkin et al. ............... 501/103 |
| 2003/0102207 A1 | 6/2003 | Wu et al. |
| 2009/0321971 A1 | 12/2009 | Brodkin et al. |
| 2010/0003630 A1 * | 1/2010 | Yamashita et al. ................ 433/8 |
| 2010/0041542 A1 * | 2/2010 | Rolf et al. ..................... 501/104 |

OTHER PUBLICATIONS

Krell, A. et al. "Transparent compact ceramics: Inherent physical issues." Optical Materials 31. Dec. 9, 2009. pp. 144-1150.

Anselmi-Tamburini, Umberto et al. "Transparent Nanometric Cubic and Tetragonal Zirconia Obtained by High-Pressure Pulsed Electric Current Sintering." Advanced Functional Materials. Revised Dec. 3, 2006 and Published online Sep. 11, 2007. pp. 3267-3273.

Winterer, M. "Nano-crystalline Ceramics Synthesis and Structure." Materials Science. 2002. Cover page, Contents pp. XVII-XIX, pp. 1-33 and 90-146, References pp. 232-249 and Index pp. 250-260.

Kawanami, O. et al. "Effects of gravity on single-wall carbon nanotubes synthesized by arc in water." Applied Physics A—Materials Science & Processing 89, 929-932. 2007 (Accepted Aug. 21, 2007; Published Sep. 14, 2007). 1 page.

Ashkarran, Ali et al. "Photocattalytic activity of Zro2 nanoparticles prepared by electrical arc discharge method in water." Science Direct—Polyhedron 29. Copyright 2010 Elsevier Ltd. Accepted Jan. 4, 2010; Available Jan. 11, 2010. pp. 1370-1374.

\* cited by examiner

NANO-CRYSTALLINE DENTAL CERAMICS

BACKGROUND AND SUMMARY

The present application relates to ceramic dental devices, such as dental crowns, veneers, bridges, implants, or dentures, and processes and materials used for making dental devices containing ceramics.

One method for the manufacture of ceramic dental devices involves providing a green-state or partially sintered dental blank that is first shaped, for example by CAD/CAM milling, and then sintered at a high temperature to produce a final dental device. Typically, such green-state material is partially sintered to form a bisque-state material that is hard enough to retain its structure while being milled, yet soft enough to allow relatively rapid shaping that does not damage the milling tool.

Such a green-state material may contain ceramic particles mixed with a binder that evaporates during the formation of the bisque-state material, leaving pores between the ceramic crystals of the bisque-state material. During solid state sintering, a reduction of free energy occurs, which is a driving force in reducing the pore size, so that the final sintered product has a shape that replicates the milled bisque-state or green-state intermediate product but is reduced in size.

One way to quantify the overall amount of pores that exist in an intermediate or final product is to measure the density of that product, as compared to a theoretical density of a ceramic material that is to form the final product, assuming that product is pore-free. Typical green-state or bisque-state materials may have a relative density that is between fifty-percent and eighty-percent, although it should be noted that in the case of green state materials the relative density includes a non-ceramic binder as well as ceramic particles, compared to the theoretical pore-free density of the final product ceramic material.

The ceramic particles that are used in the green state material may be manufactured by hydrolyzing an aqueous metal salt solution, such as a solution of zirconia, to obtain hydrous zirconia sol having an average particle size of from 0.05 to 0.3 micron. This zirconia sol can then be mixed for example with an yttrium compound, after which the mixture is calcined at a temperature ranging from 800° C. to 1100° C., followed by ball milling the calcined matter. The crystallite grains produced by this process may have a size as small as ten nanometers, but are not present individually but rather agglomerated during hydrolysis and calcining, which sinters the particles at elevated temperatures. Even after ball milling to break up the agglomerated particles, the particle size is at least about double the crystallite size, and typically greater than twenty nanometers, while some of the particles that make up the powder commonly exceed one hundred nanometers.

U.S. Published Application No. 2009/0321971 to Brodkin et al. teaches that the widely divergent size of the particles that form such a ceramic powder is advantageous for hand-built dental restorations as well as for feedstock for CAD/CAM restorations. As also noted in that application, although pore size is reduced during sintering, the pores typically are not completely removed, so that a final product such as a dental crown or other prosthesis may contain a multitude of microscopic pores. The pores may reflect light to an extent that for some dental ceramics the prosthesis has lower translucence than a natural tooth.

As noted in U.S. Pat. No. 4,520,114 to David, ball milling induces a stress that transforms tetragonal zirconia, which has good strength and resistance to cracking, to a monoclinic phase crystal structure, which has lower strength and much lower resistance to cracking. As the ball milling breaks large particles into smaller particles, the most complete transformation away from tetragonal zirconia occurs on particle surfaces that are created by the breaking. In addition, the surface portions of large particles are most directly affected by the pressure of the ball milling even without breakage, and for this reason also the surface portions are the most completely transformed from tetragonal zirconia to monoclinic zirconia.

Thus, the transformation to monoclinic phase zirconia becomes more complete as the particles are made smaller and the surface portions extend throughout the particles. The zirconia particles described in David are significantly larger than those of Brodkin et al., and for the reasons mentioned above, zirconia particles produced by hydrolysis, calcining and ball milling may have little or no tetragonal zirconia when the particle size is significantly less than fifty nanometers. Such a transformation to monoclinic phase zirconia is not reversed in bisque-state zirconia, and is only partly reversed at typical sintering temperatures of 1000° C.-1200° C. Tetragonal zirconia has high flexural strength, as mentioned above, because it resists crack propagation by transforming to monoclinic zirconia due to stress induced by a crack, absorbing energy and changing the crystal lattice along which the crack would otherwise propagate.

Instead of producing dental ceramic powder by the conventional "top-down" approach of hydrolysis, calcining and ball milling, the present inventors have employed a "bottom-up" approach of producing dental ceramic crystals as individual nanoscale particles that do not need to be broken down. The dental ceramic particles created by this approach can be made much smaller than is conventional, and issues such as transformation of the particles from tetragonal zirconia to monoclinic zirconia are avoided. The dental ceramic particles created by this approach can also be more uniform in both shape and size distribution. Cylindrical and spherical particles can be manufactured by this approach, whereas the prior art dental ceramic particles were generally neither. In addition, the smaller size of the tetragonal zirconia particles increases optical translucence by reducing scattering from birefringence, and the small average size and tight distribution of sizes can essentially eliminate pores in a sintered product. Various dental ceramic particles and powders can be made by this approach, in addition to tetragonal zirconia.

In one embodiment, dental ceramic particles are created as a vapor of the particles which is then collected as a powder. In one embodiment, dental ceramic particles are created by vaporization of solid ceramic bodies. In one embodiment, dental ceramic particles are created by vaporization and/or ionization of solid metal bodies, and the subsequent reaction of vaporized metal atoms and/or ions with oxygen, nitrogen and/or carbon atoms or molecules containing such atoms.

In one embodiment, ultrafine dental ceramic particles are created by a chemical vapor synthesis (CVS) system. In one embodiment, ultrafine dental ceramic particles are created by a physical vapor synthesis (PVS) system. In one embodiment, ultrafine dental ceramic particles are created by a combined CVS and PVS system. In one embodiment, ultrafine dental ceramic particles are created by an arc in liquid system.

In one embodiment, a dental device is disclosed comprising a solid body made of dental ceramic molecules including at least eighty mass percent crystals having a mean size of between one nanometer and one hundred nanometers, and a standard deviation from the mean size that is less than twenty percent of the mean size, the body having a shape of a dental prosthesis, having a flexural strength that is between six hundred mega-Pascals and two thousand mega-Pascals, wherein a one millimeter thickness of the body has an optical transmittance of between twenty percent and ninety-five percent for a wavelength of light that is between four hundred nanometers and seven hundred nanometers.

In one embodiment, a dental device is disclosed comprising a solid body including at least eighty mass percent dental ceramic molecules in the form of crystals having a length and a width such that an aspect ratio of the length to the width is at least two to one, the body having a shape of a dental prosthesis, having a flexural strength that is between six hundred mega-Pascals and two thousand mega-Pascals, wherein a one millimeter thickness of the body has an optical transmittance of between twenty percent and ninety-five percent for a wavelength of light that is between four hundred nanometers and seven hundred nanometers.

In one embodiment, a dental device is disclosed comprising a solid body containing at least forty atomic percent tetragonal zirconium oxide crystals having a mean size of between one nanometer and one hundred nanometers, and a standard deviation from the mean size that is less than twenty percent of the mean size, the body shaped in the form of a dental prosthesis and characterized by having a flexural strength between eight hundred mega-Pascals and two thousand mega-Pascals, and having an optical transmittance for a one millimeter thickness of between thirty-five percent and ninety-five percent for a wavelength of light that is between four hundred nanometers and seven hundred nanometers.

In one embodiment, a dental device is disclosed comprising a solid body containing at least forty mass percent tetragonal zirconia in the form of crystals having a length and a width such that the length is at least twice as large as the width, the body shaped in the form of a dental prosthesis and characterized by having a flexural strength between eight hundred mega-Pascals and two thousand mega-Pascals, and having an optical transmittance for a one millimeter thickness of between thirty-five percent and ninety-five percent for a wavelength of light that is between four hundred nanometers and seven hundred nanometers.

In one embodiment, a dental device is disclosed comprising a solid body made of a compressed powder containing at least forty mass percent tetragonal zirconia, the body shaped in the form of a dental blank and having a density that is between thirty percent and eighty percent of a theoretical maximum density of the body, wherein the powder is made of particles having a mean size in a range between one-half nanometer and thirty nanometers, and a standard deviation from the mean size that is less than twenty percent of the mean size.

In one embodiment, a dental device is disclosed comprising a solid body made of a compressed powder containing at least eighty mass percent tetragonal zirconia, the body shaped in the form of a dental blank, the powder made of particles having a maximum size of twenty nanometers.

In one embodiment, a dental device is disclosed comprising a solid body made of a compressed powder of dental ceramic particles, wherein the dental ceramic particles include zirconium oxide, aluminum oxide, hafnium oxide, niobium oxide or yttrium oxide, the body shaped in the form of a dental blank and the particles having a mean size of between one-half nanometer and ten nanometers, and a standard deviation from the mean size that is less than twenty percent of the mean size.

In one embodiment, a dental device is disclosed comprising a solid body made of a compressed powder containing dental ceramic nanorods, the body shaped in the form of a dental blank and characterized by having a density that is between thirty percent and eighty percent of a theoretical maximum density of the body.

In one embodiment, a dental device is disclosed comprising a solid body made of a compressed powder containing at least eighty mass percent dental ceramic particles having a length to width aspect ratio of at least two to one, the body shaped in the form of a dental blank and characterized by having a density that is between forty percent and eighty percent of a theoretical maximum density of the body.

In one embodiment, a dental device is disclosed comprising a bisque-state solid body containing at least eighty mass percent tetragonal zirconium oxide crystals having a mean size of between one nanometer and one fifty nanometers, and a standard deviation from the mean size that is less than twenty percent of the mean size, the body shaped in the form of a dental blank and having a density that is between fifty percent and ninety percent of a theoretical maximum density of the body.

In one embodiment, a dental device is disclosed comprising a bisque-state solid body containing at least eighty mass percent tetragonal zirconium oxide crystals having a length to width aspect ratio of at least two to one, the body shaped in the form of a dental blank and having a density that is between fifty percent and ninety percent of a theoretical maximum density of the body.

In one embodiment, a dental device is disclosed comprising a bisque-state solid body made of dental ceramic crystals containing at least fifty mass percent zirconium oxide, aluminum oxide, hafnium oxide, tantalum oxide, titanium oxide, niobium oxide, or yttrium oxide having a length to width aspect ratio of at least two to one, the body shaped in the form of a dental blank and having a density that is between fifty percent and ninety percent of a theoretical maximum density of the body.

In one embodiment, a dental device is disclosed comprising a solid body made of a powder mixed with a binder, the body shaped in the form of a dental blank, the powder containing at least forty mass percent tetragonal zirconia, wherein the powder is made of particles having a mean size in a range between one-half nanometer and thirty nanometers, and a standard deviation from the mean size that is less than twenty percent of the mean size.

In one embodiment, a dental device is disclosed comprising a solid body made of a powder mixed with a binder, the body shaped in the form of a dental blank, the powder containing at least eighty mass percent tetragonal zirconia, the powder made of particles having a maximum size of twenty nanometers.

In one embodiment, a dental device is disclosed comprising a solid body made of a powder mixed with a binder, the body shaped in the form of a dental blank, the powder made of dental ceramic particles, wherein the dental ceramic particles include zirconium oxide, aluminum oxide, hafnium oxide, niobium oxide or yttrium oxide, and the dental ceramic particles have a mean size of between one-half nanometer and ten nanometers, with a standard deviation from the mean size that is less than twenty percent of the mean size.

In one embodiment, a dental device is disclosed comprising a solid body made of a powder mixed with a binder, the powder containing dental ceramic nanorods, the body shaped in the form of a dental blank and having a density that is between twenty percent and seventy percent of a theoretical maximum density of the body.

In one embodiment, a dental device is disclosed comprising a solid body made of a powder mixed with a binder, the powder containing at least eighty mass percent dental ceramic particles having a length to width aspect ratio of at least two to one, the body shaped in the form of a dental blank and having a density that is between twenty percent and seventy percent of a theoretical maximum density of the body.

In one embodiment, a method for making a dental device is disclosed comprising: forming a vapor containing dental ceramic particles of at least one oxide, nitride, carbide, oxynitride or carbon-nitride of zirconium, hafnium, aluminum, niobium, tantalum, titanium or yttrium; collecting the dental ceramic particles as a powder having a maximum particle diameter of between one nanometer and ten nanometers; and forming the powder into a dental blank. In one embodiment, the method for making a dental device further comprises forming the blank into a shape of a dental prosthesis. In one embodiment, the method for making a dental device further comprises sintering the prosthesis.

DETAILED DESCRIPTION

Figure 1:
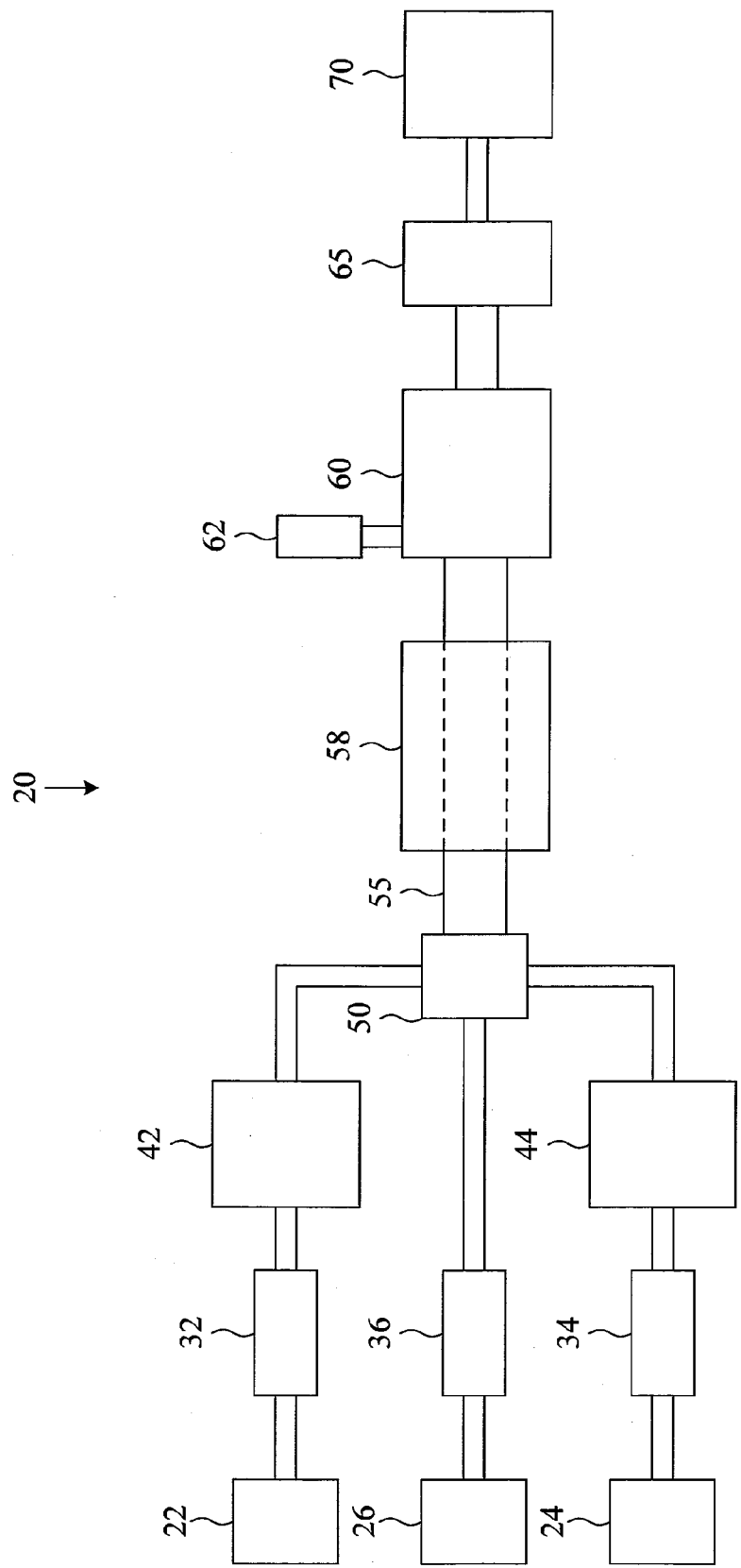
FIG. 1 is a schematic block diagram of a chemical vapor synthesis (CVS) system that can be used to create nano-crystalline dental ceramic powder.

FIG. 1 is a block diagram of a chemical vapor synthesis (CVS) system, shown generally at 20, which can be used to create a nano-crystalline dental ceramic powder. In exemplary system 20, helium or another inert gas (e.g., argon) is provided by sources 22 and 24, the flow of the gas being controlled by respective mass flow controllers 32 and 34, to respective bubblers 42 and 44, which contain metal organic (MO) precursor liquids or solids. The bubblers 42 and 44 output MO precursor vapors along with helium gas to vapor mixer 50. MO precursor vapors may be formed by vapors from liquids or subliming solids. Vapors from MO precursor liquids can be created by heating a liquid in a bubbler or direct injection of the MO liquid by an ultrasonic nebulizer. A reactive gas such as oxygen is provided by source 26, the flow of which is controlled by mass flow controller 36, to also flow into vapor mixer 50.

The mixture of MO vapors, helium and oxygen gases flows through hot wall reactor tube 55, which is heated by heater 58. Hot wall reactor tube 55 causes the metal and organic portions of the MO vapor or vapors to disassociate into volatile hydrocarbons or halides and an inorganic metal element or elements, or metallic ions. The metal element, elements or ions then react with oxygen atoms, molecules or ions to form dental ceramic molecules. The gas phase ceramic molecules and/or molecular particles may collide with each other growing into atomically ordered molecular clusters, which may for example be between 0.1 nm and 50 nm in diameter, during transport through the reactor tube. Note that these particles of atomically ordered molecular clusters, also called crystallites, are significantly smaller than the particles formed by agglomerates of crystallites produced by conventional hydrolysis. In addition, individual crystallites particles are formed according to this embodiment, rather than conventional particles made of agglomerated crystallites. Moreover, a powder containing these vapor-reacted particles can be made with a much tighter distribution of sizes than conventional liquid-reacted dental ceramic particles, so that essentially all of the particles in the powder are, in one exemplary embodiment, substantially spherical in shape and less than 20 nm in diameter. The term substantially spherical includes particles having a major axis that is no more than five percent larger than their minor axis, whereas in one embodiment a majority of the particles have a major axis that is no more than one percent larger than their minor axis, and in another embodiment essentially all of the particles have a major axis that is no more than one percent larger than their minor axis. In another exemplary embodiment, essentially all of the particles in the powder are substantially spherical in shape and less than 10 nm in diameter. In another exemplary embodiment, the particles in the powder are substantially cylindrical nanorods, and essentially all of the particles in the powder are less than 10 nm in diameter and less than 100 nm in length.

The MO precursors in bubbler 42 preferably contain, as part of the MO molecules in the liquid, a metal element that can be used to form dental ceramic molecules. Dental ceramic molecules that can be formed in this embodiment include oxides such as zirconium oxide ($ZrO_2$, sometimes called zirconia), hafnium oxide ($HfO_2$), niobium oxide ($Nb_2O_5$), ($Nb_2O_3$), tantalum oxide ($Ta_2O_5$), titanium oxide ($TiO_2$), aluminum oxide ($Al_2O_3$), yttrium oxide ($Y_2O_3$), iron oxide ($Fe_2O_3$), ($Fe_3O_4$), (FeO), terbium oxide ($Tb_4O_7$), praseodymium oxide ($Pr_2O_3$), chromium oxide ($Cr_2O_3$), vanadium oxide($V_2O_5$), cobalt oxide (CoO), ($Co_2O_3$), nickel oxide (NiO), cerium oxide ($CeO_2$), europium oxide ($Eu_2O_3$) and copper oxide (CuO). In one embodiment, the dental ceramic particles are primarily tetragonal zirconia, and may be at least eighty mass percent zirconia and between one-half mass percent and ten mass percent yttria.

The MO precursor liquid in bubbler 44 preferably contains, as part of the MO molecules in the liquid, a different metal element from that found in bubbler 42. Bubbler 42 and bubbler 44 may each contain, as part of the MO molecules in each bubbler, more than one metal element that can be used to form dental ceramic molecules. Only one bubbler and only one MO precursor liquid may instead be used, or one or more additional bubblers containing additional MO precursor liquids or solids may be provided.

The gaseous dental ceramic molecules and/or clusters of molecules, along with other gaseous byproducts, flow while monitored by a baratron pressure transducer 62 into a powder collection system 60, where the dental ceramic powder is collected. A cold trap 65, which may for example be cooled by liquid nitrogen, is provided to remove gaseous byproducts, while a vacuum pump 70 provides a pressure differential that promotes the flow of gases through the system 20.

Exemplary compositions of dental ceramic molecules that can be formed as solid state ceramic dental prostheses include the following: composition 1: zirconia (99.5%-90%) and yttria (0.5%-10%), at. %; composition 2: zirconia(99.49%-90%), yttria(0.5%-9%) and alumina (0.001%-1%), at. %; composition 3: zirconia(99.99%-90%) and alumina (0.001%-10%), at. %; composition 4: zirconia(99.49%-89%), yttria(0.5%-9%), alumina (0.001%-1%) and iron oxide (0.005%-1.0%), at. %; composition 5: zirconia(99.49%-89%), yttria(0.5%-9%), alumina (0.001%-1%) and terbium oxide (0.005%-1.0%), at. %.

MO precursor liquids that can be used to form zirconium oxide ($ZrO_2$) include: tetra(tert-butoxide)zirconium (ZTBO), zirconium acetylacetonate, zirconium isopropoxide (ZIP), zirconium n-propoxide (ZNP), zirconium 2-methyl-2-butoxide, zirconium n-butoxide, methylcyclopentadienylZirconiumMethoxyMethyl, zirconium hydroxyl acetate, tetrakis(dimethylamino)zirconium, tetrakis(2,2,6,6-tetramethylheptane-3,5-dionato)zirconium, tris(isopropoxy)mono(2,2,6,6-tetramethylheptane-3,5-dionato)zirconium, tetrakis(ethylmethylamino)zirconium (TEMAZ), tetrakis(diethylamino)zirconium, bis(tert-butoxy)bis(1-methoxy-2-methyl-2-propoxy)zirconium, bis(methyl-η5-cyclopentadienyl)methoxymethylzirconium-Zirconium, tris(2,2,6,6-tetramethylheptane-3,5-dionato)yttrium and tris(1-methoxy-2-methyl-2-propoxy)yttrium.

MO precursor liquids that can be used to form hafnium oxide ($HfO_2$) include: tetrakis(tert-butoxy)hafnium, tetrakis(diethylamino)hafnium, tetrakis(dimethylamino)-hafnium, tetrakis(ethylmethylamino)hafnium, tetrakis(1-methoxy-2-methyl-2-propoxy)hafnium, bis(tert-butoxy)bis(1-methoxy-2-methyl-2-propoxy)hafnium, hafnium tetrachloride, bis(methyl-η5-cyclopentadienyl)dimethylhafnium and bis(methyl-η5-cyclopentadienyl)methoxymethylhafnium.

MO precursor liquids that can be used to form niobium oxide ($N_2O_5$), ($Nb_2O_3$) include: pentakis(ethoxy)niobium and pentakis(butoxy)niobium.

MO precursor liquids that can be used to form tantalum oxide ($Ta_2O_5$) include: pentakis(dimethylamino)-tantalum, pentakis(ethoxy)tantalum, pentakis(butoxy)-tantalum, tetraethoxy(dimethylaminoethoxy)tantalum, tris(diethylamino)(tert-butylimido)tantalum and tantalum pentachloride.

MO precursor liquids that can be used to form titanium oxide ($TiO_2$) include: tetra titanium iso-propoxide, tetraisopropyl orthotitanate, titanium tetrachloride, tetrakis(diethylamino)titanium, tetrakis(tert-butoxy)titanium, tetrakis(1-methoxy-2-methyl-2-propoxy)titanium and bis(isopropoxy)bis(1-methoxy-2-methyl-2-propoxy)titanium.

MO precursor liquids that can be used to form aluminum oxide ($Al_2O_3$) include: aluminum-isopropoxide, trimethylaluminium, dimethylaluminium hydride and diethylaluminium ethoxide.

MO precursor liquids that can be used to form yttrium oxide ($Y_2O_3$) include: yttrium methoxyethoxide, yttrium iso-propoxide, yttrium (III) butoxide, tris(2,2,6,6-tetramethylheptane-3,5-dionato)yttrium and tris(1-methoxy-2-methyl-2-propoxy)yttrium.

MO precursor liquids that can be used to form iron oxide ($Fe_3O_4$), (FeO) ($Fe_2O_3$) include: bis(η5-cyclopentadienyl)iron.

Instead of or in addition to oxygen gas, nitrogen gas may be provided to vapor mixer 50 or a mixture of oxygen and nitrogen. Dental ceramic molecules that can be formed in this embodiment include nitrides and oxy-nitrides such as aluminum nitride and aluminum oxynitride, silicon nitride and silicon oxynitrde, titanium nitride and titanium oxynitride, zirconium nitride and zirconium oxynitride, etc.

Instead of or in addition to nitrogen gas, hydrogen-carbon (e.g., methane) gas may be provided to vapor mixer 50. Dental ceramic molecules that can be formed in this embodiment include carbides and carbon-nitrides such as boron carbide, silicon carbide, titanium carbide, aluminum carbide, and associated carbon-nitrides.

Instead of or in addition to oxygen gas, water vapor through a bubbler with or without a helium gas carrier may be provided to vapor mixer 50 for forming dental ceramic oxides.

Instead of or in addition to oxygen gas, diatomic oxygen, ozone or $O_3$ gas may be provided to vapor mixer 50 for forming dental ceramic oxides.

In one embodiment, hot wall reactor tube 55 may have an interior surface that is made of quartz silica, alumina, zirconia or silicon carbide, for example. In one embodiment, the reactor tube 55 may have an inner diameter of between 10 mm and 50 mm, although larger and smaller diameters may be possible, with a preferred diameter of about 20 mm. Similarly, the reactor tube 55 may have length of between 10 mm and 300 mm, although larger and smaller lengths may be possible, with a preferred length of about 20 mm. In one embodiment, the temperature of the reactor tube 55 may be between 500° C. and 1500° C., preferably about 1000° C., as determined for example by the interior temperature of the heater 58. In one embodiment, the pressure inside the reactor tube 55 may be between 0.1 Torr and 50 Torr, and preferably is about 7-9 Torr.

Figure 2:
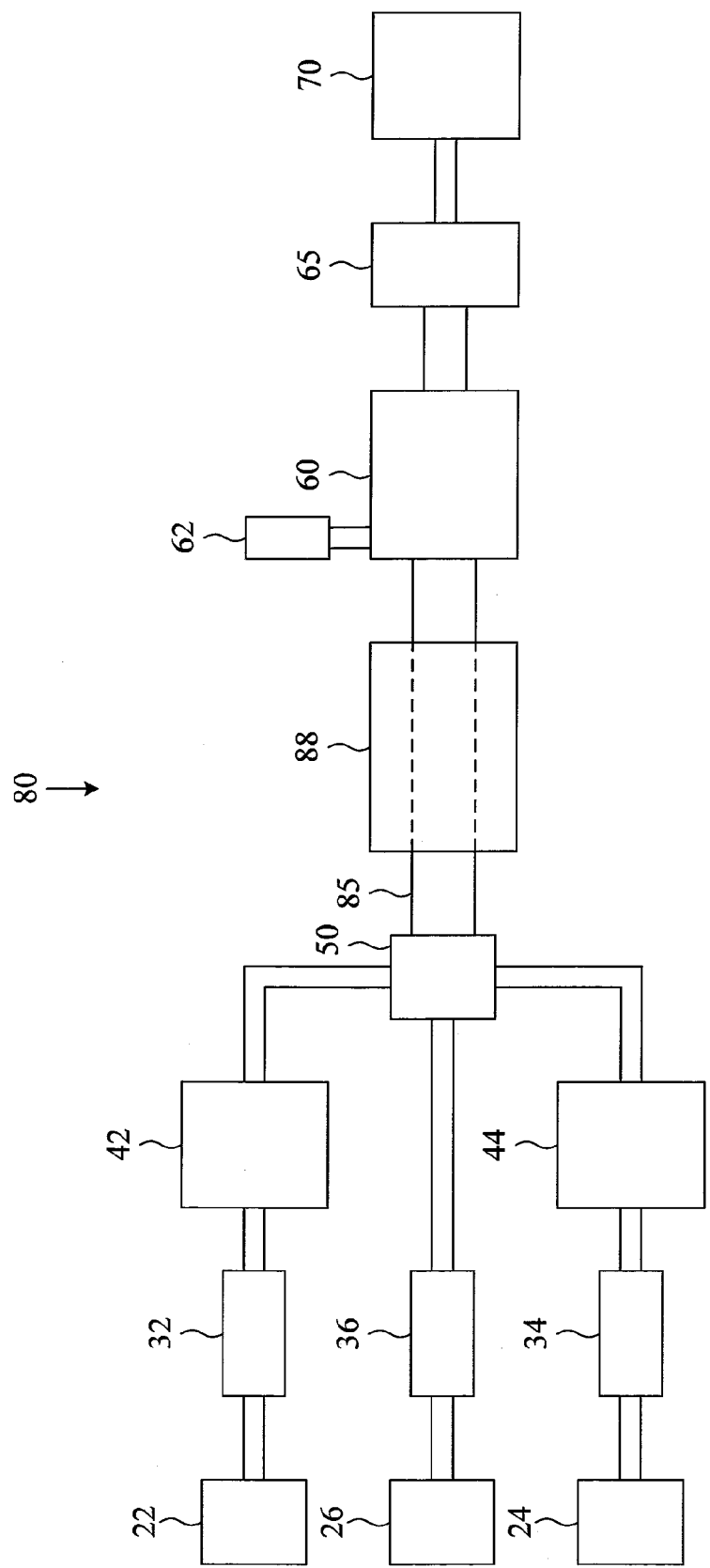
FIG. 2 is a schematic block diagram of a CVS system like that of FIG. 1 but having a plasma-enhanced reactor tube.

Instead of or in addition to the thermally enhanced reaction produced by hot wall reactor tube 55, a plasma enhanced reaction of MO precursor vapors and other reactive species may be used to produce dental ceramic particles. FIG. 2 shows a CVS system 80, including a plasma enhanced reactor tube 85, which can be used to create a nano-crystalline dental ceramic powder. Operably coupled to plasma enhanced reactor tube 85 is a plasma generator 88.

Plasma generator 88 can, in one exemplary embodiment, provide electromagnetic radiation to the interior of reactor tube 85, which can ionize reactants in the tube, such as MO precursor vapors and/or gases of oxygen, nitrogen or hydrogen-carbon (e.g., methane). For example, a radio frequency (RF) radiation of about 13.5 MHz may be used for capacitive or inductive plasma discharges, in which an ionizing field is created in the reaction chamber using, for example, conductive plates or an inductive coil. Alternatively, a microwave frequency of, for example, 2450 MHz can be used. In another embodiment, plasma generator 88 may include an ion beam generator, such as a hot filament or plasma source Kaufman ion gun.

Figure 3A:
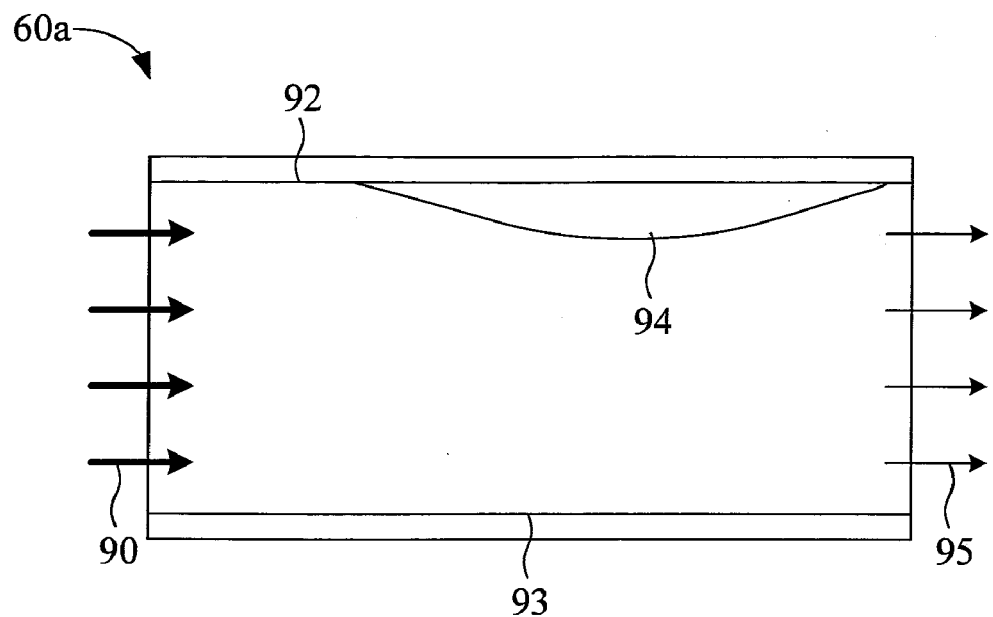
FIG. 3A is a schematic block diagram of a powder collection system that employs thermophoresis.

As mentioned above, the gaseous dental ceramic particles can be collected near an outflow end of the reactor tube 55 by a particle or powder collection system 60. FIG. 3A shows an embodiment of a powder collection system 60a that employs thermophoresis to collect dental ceramic nanoparticles. Thick arrows 90 represent a mixture of dental ceramic particles, gases such as helium and any gaseous byproducts of the reaction that formed the dental ceramic particles, entering powder collection system 60*a* from the reaction tube or chamber, not shown. A cold inner surface 92 of the particle collection system 60*a* is disposed opposite to a heated inner surface 93, with surfaces 92 and 93 generally orthogonal to the flow of gases and nanoparticles through system 60*a*. The hot surface 93 may be at a temperature of between about 20° C. and 400° C., which provides kinetic energy to any nearby nanoparticles and gaseous species, driving them toward the cold surface 92. The cold surface 92 may be at a temperature of between about −200° C. and 200° C., which condenses the dental ceramic nanoparticles so that they can be collected as a powder 94. Thin arrows 95 represent the gases and gaseous byproducts, from which the dental ceramic nanoparticles have been removed, exiting powder collection system 60*a*. The thermophoretic force can be considered to be a result of the net gaseous ballistic kinetic energy transfer to another gaseous species (aerosol or nanoparticle), resulting in a net spatial drift direction of the nanoparticle toward the lower energy surface or cold surface.

Figure 3B:
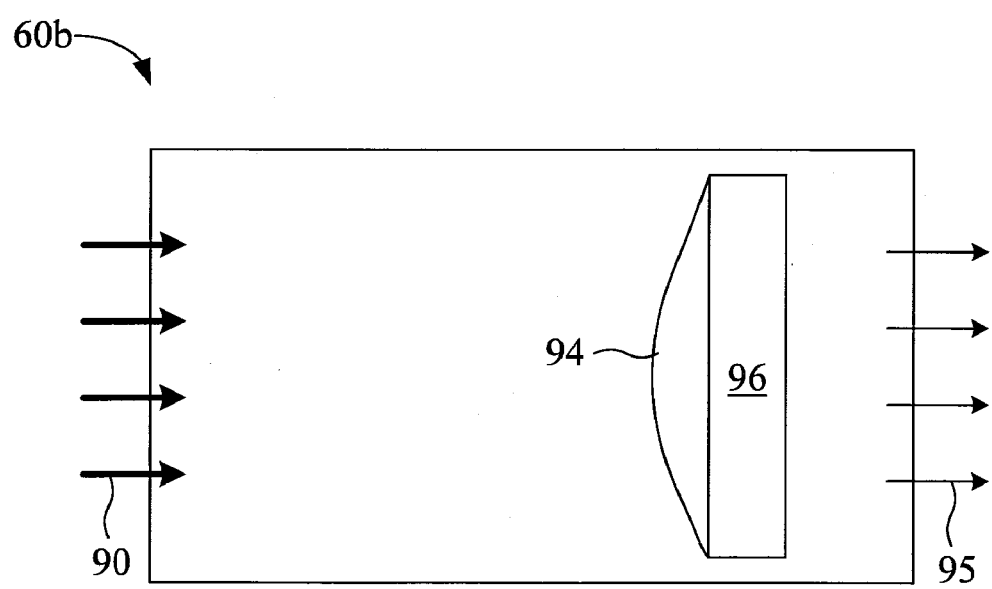
FIG. 3B is a schematic block diagram of a powder collection system that employs a cold trap.

FIG. 3B shows an embodiment of a powder collection system 60*b* that employs a cold trap 96 to collect dental ceramic nanoparticles. Much as described above, thick arrows 90 represent a mixture of dental ceramic particles, gases such as helium and any gaseous byproducts of the reaction that formed the dental ceramic particles, entering powder collection system 60*b* from the reaction tube or chamber, not shown. The particles encounter cold trap 96, which may for example be cooled with liquid nitrogen, causing dental ceramic nanoparticles 94 to collect on the cold trap. Thin arrows 95 represent the gases and gaseous byproducts, from which the dental ceramic nanoparticles have been removed, exiting powder collection system 60*b*. The cold trap 96 may have a temperature in a range between −200 C. and 10 C. The lower temperature surface of the cold trap 96 promotes condensation of the energetic nanoparticles by increasing the sticking coefficient by transferring the particle energy to the cold collection surface.

Figure 3C:
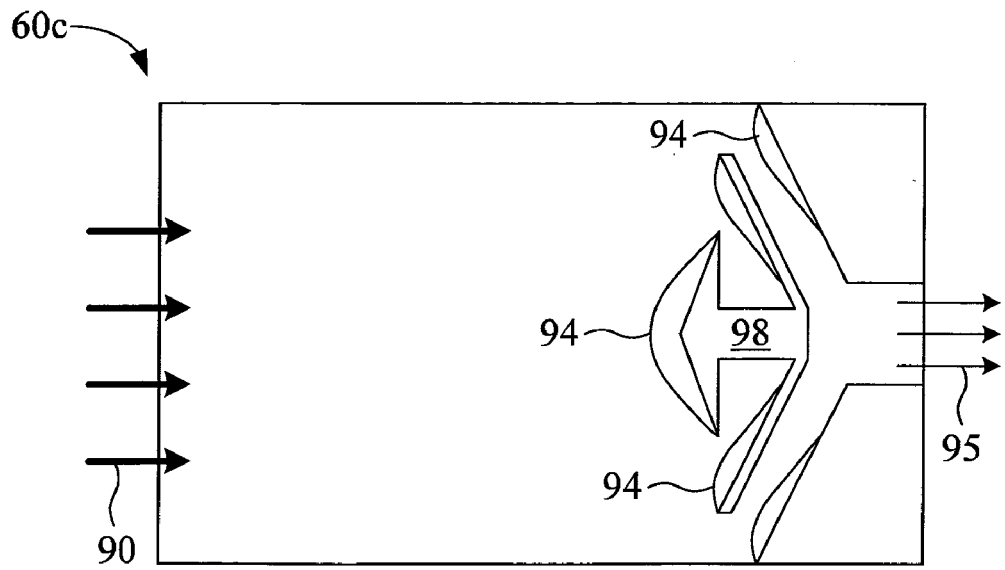
FIG. 3C is a schematic block diagram of a powder collection system that employs a physical trap.

FIG. 3C shows an embodiment of a powder collection system 60*c* that employs a physical trap 98 to collect dental ceramic nanoparticles. Much as described above, thick arrows 90 represent a mixture of dental ceramic particles, gases such as helium and any gaseous byproducts of the reaction that formed the dental ceramic particles, entering powder collection system 60*c* from the reaction tube or chamber, not shown. The particles encounter physical trap 98, which has a number of surfaces that are disposed in the path of the flow of particles and gases, depositing the particles on the surfaces and redirecting the gases, causing dental ceramic nanoparticles 94 to collect on the physical trap. Physical trap 98 collects nanoparticles by physical condensation on the collection surface by the initial surface roughness and texture. The physical trap 98 collection efficiency increases as the material self collects by the growth texture of the nanoparticles and forms a self assembled growth habit. Harvesting the dental ceramic powder 94 may leave at least a surface layer of dental ceramic particles on the physical trap collection surfaces, providing a template for future powder collection. Thin arrows 95 represent the gases and gaseous byproducts, from which the dental ceramic nanoparticles have been removed, exiting powder collection system 60*c*.

Figure 3D:
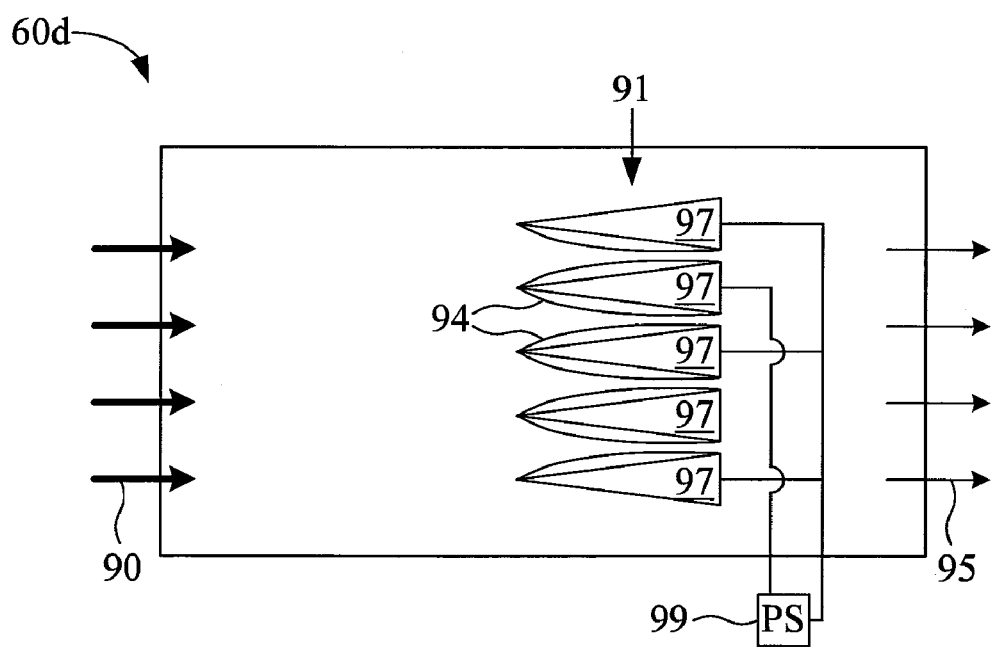
FIG. 3D is a schematic block diagram of a powder collection system that employs an electrical trap.

FIG. 3D shows an embodiment of a powder collection system 60*d* that employs an electrical trap 91 to collect dental ceramic nanoparticles. Much as described above, thick arrows 90 represent a mixture of dental ceramic particles, gases such as helium and any gaseous byproducts of the reaction that formed the dental ceramic particles, entering powder collection system 60*d* from the reaction tube or chamber, not shown. The particles encounter electrical trap 91, which has a number of electrodes 97 that are oppositely charged compared to adjacent electrodes 97, due to a static or oscillating electric field provided by power supply (PS) 99, causing dental ceramic nanoparticles 94 to collect on the electrode surfaces. Electrical trap 91 collects nanoparticles by physical condensation on the collection surface by the initial surface roughness and texture. The physical trap 98 collection efficiency increases as the material self collects by the growth texture of the nanoparticles and forms a self assembled growth habit. Harvesting the dental ceramic powder 94 may leave at least a surface layer of dental ceramic particles on the physical trap collection surfaces, providing a template for future powder collection. Thin arrows 95 represent the gases and gaseous byproducts, from which the dental ceramic nanoparticles have been removed, exiting powder collection system 60*c*.

Figure 4:
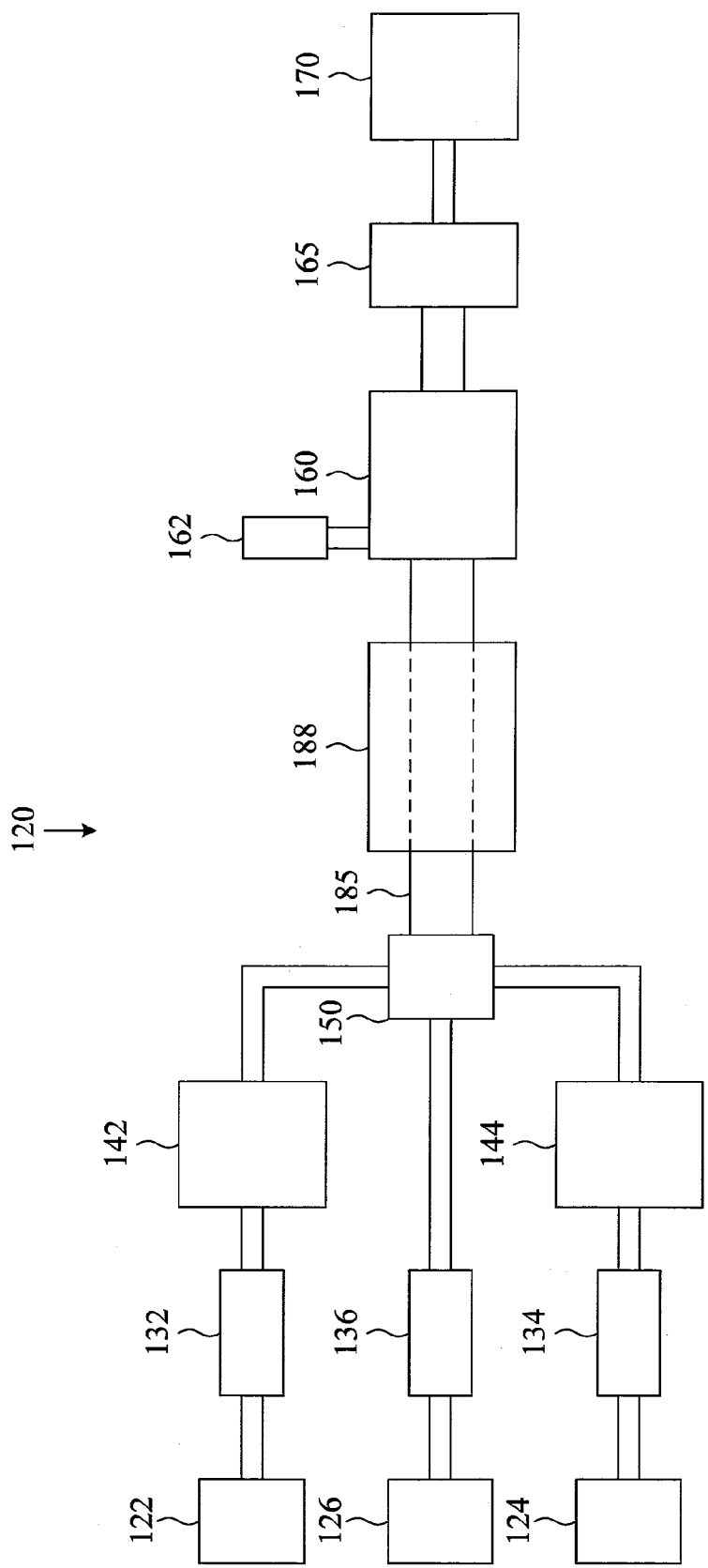
FIG. 4 is a schematic block diagram of a physical vapor synthesis (PVS) system that can be used to create nano-crystalline dental ceramic powder.

FIG. 4 is a block diagram of a physical vapor synthesis (PVS) system, shown generally at 120, which can be used to create a nano-crystalline dental ceramic powder. In exemplary system 120, helium or another inert gas (e.g., argon) may optionally be provided by sources 122 and 124, the flow of the gas being controlled by respective mass flow controllers 132 and 134, to respective evaporation chambers 142 and 144, which contain solid metal or ceramic targets. The chambers 142 and 144 include means for vaporizing the solid targets to output metallic and/or ceramic vapors, optionally along with helium or another inert gas to vapor mixer 150.

Solid targets that may be vaporized in evaporation chambers 142 and 144 include metals, metallic oxides, metallic carbides, metallic nitrides or metallic silicides and metallic carbo-nitrides of the following: zirconium, titanium, aluminum oxide, yttrium, iron, terbium, praseodymium, chromium, vanadium, niobium, tantalum, cobalt, nickel, cerium, europium, copper and hafnium.

Mechanisms and techniques that can be used to vaporize such targets are generally known in the semiconductor industry, where they may be used for physical vapor deposition. Examples of mechanisms and techniques that can be used to vaporize a solid metallic or ceramic targets in chambers 142 and 144 include: resistive evaporation, in which the target material is heated to a high vapor pressure by electrically resistive heating in a reduced pressure environment; electron beam evaporation, in which the target material is heated to a high vapor pressure by electron bombardment in a reduced pressure environment; sputter deposition, in which a glow plasma discharge, commonly localized around the target by a magnet, bombards the target so that some of the target is dislodged as a vapor; cathodic arc evaporation, in which a high power and high current arc directed at the target material blasts away some into a vapor; and pulsed laser evaporation, in which a high power laser ablates material from the target into a vapor.

Oxygen or another reactive gas (e.g., nitrogen or methane) may be provided by source 126, the flow of which is controlled by mass flow controller 136, to also flow into vapor mixer 150. The metal and/or ceramic vapors from the target materials, optionally mixed with inert and/or reactive gases such as helium and oxygen, flow through tube 185, which may be operably coupled to plasma generator 188, providing ionization of metals or gases and subsequent reaction as discussed above. The gas phase ceramic molecules and/or molecular particles may collide with each other, growing into atomically ordered molecular clusters, which may for example be between 0.1 nm and 50 nm in diameter, during transport through the reactor tube.

As noted above, these particles of atomically ordered molecular clusters, also called crystallites, are significantly smaller than the particles formed by agglomerates of crystallites produced by conventional hydrolysis. In addition, individual crystallites particles are formed according to this embodiment, rather than conventional particles made of agglomerated crystallites. Moreover, a powder containing these vapor-reacted particles can be made with a much tighter distribution of sizes than conventional liquid-reacted dental ceramic particles, so that essentially all of the particles in the powder are, in one exemplary embodiment, substantially spherical in shape and less than 10 nm in diameter. In another exemplary embodiment, the particles in the powder are substantially cylindrical nanorods, and essentially all of the particles in the powder are less than 10 nm in diameter and less than 200 nm in length.

The gaseous dental ceramic molecules and/or clusters of molecules, along with other gaseous byproducts, flow while monitored by a baratron pressure transducer 162 into a powder collection system 160, where the dental ceramic powder is collected. Powder collection system 160 may, for example, be any of the powder collection systems 60a, 60b, 60c or 60d described above with reference to FIGS. 3A-3D, respectively. A cold trap 165, which may for example be cooled by liquid nitrogen, can be provided to remove gaseous byproducts, while a vacuum pump 170 provides a pressure differential that promotes the flow of gases through the system 120. For the situation in which vaporized metallic or ceramic molecules are transported through system 120 at least partly due to convection of an inert gas, the cold trap 165 may be employed to condense and collect the gaseous dental ceramic molecules and/or clusters of molecules.

In one embodiment, a dental ceramic powder production system may combine CVS and PVS, with CVS used for main constituents, such as zirconia, for which MO precursors are easily available, and PVS for minority elements, such as cerium oxide or terbium oxide, for which MO precursors may not be easily available. Such a system may also be employed to allow formation of a mix of ceramic oxides and nitrides, for example, where the oxides are CVS produced and oxygen reacted, and the nitrides are produced from ceramic nitride targets. Similarly, such a CVS/PVS system can be used to create a vapor state mix of ceramic oxides and carbides, or nitrides and carbides, that might otherwise be difficult to mix, and the resulting novel nanocrystalline particle mix can be used to form novel green state, bisque state and sintered dental ceramic compositions.

Figure 5:
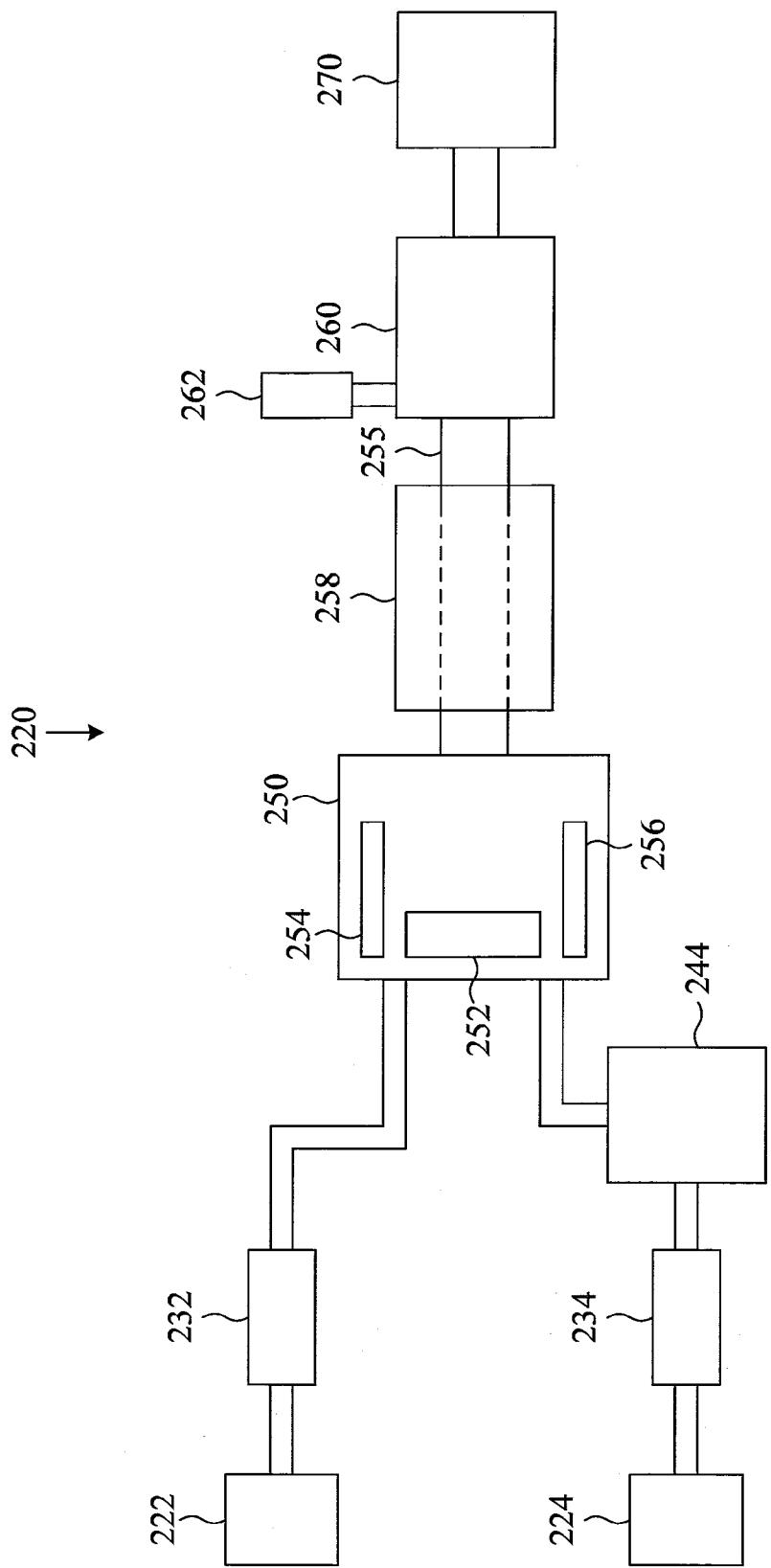
FIG. 5 is a schematic block diagram of source portions of a combined CVS and PVS system that can be used to create nano-crystalline dental ceramic powder.

FIG. 5 is a block diagram of a combined CVS/PVS system, shown generally at 220, which can be used to create a nanocrystalline dental ceramic powder. In exemplary system 220, oxygen or another reactive gas (e.g., nitrogen) flows from oxygen source 222 to chamber 250, controlled by mass flow controller 232. Helium or another inert gas (e.g., argon) flows from source 224 to bubbler 244, which contains at least one MO precursor liquid, the flow of the inert gas being controlled by mass flow controller 234. From bubbler 244 the inert gas and MO precursor vapors flow to chamber 250, which contains a mechanism to evaporate a solid metal or ceramic target 252. In this example, target 252 is an anode, so that cathodes 254 and 256 cause an electric arc that evaporates part of target 252. The metal or ceramic vapor from target 252 mixes with the oxygen from source 222 and the MO precursor gas from bubbler 244, and the mixture is output to reactor tube 255, which is coupled to reactor mechanism 258, which in turn may use heat and/or electromagnetic energy to disassociate the MO vapors and stimulate formation of ceramic molecules. The gaseous dental ceramic molecules and/or clusters of molecules, along with other gaseous byproducts, flow while monitored by a baratron pressure transducer 262 into a powder collection system 260, where the dental ceramic powder is collected. A vacuum pump 270 provides a pressure differential that promotes the flow of gases through the system 220.

Figure 6:
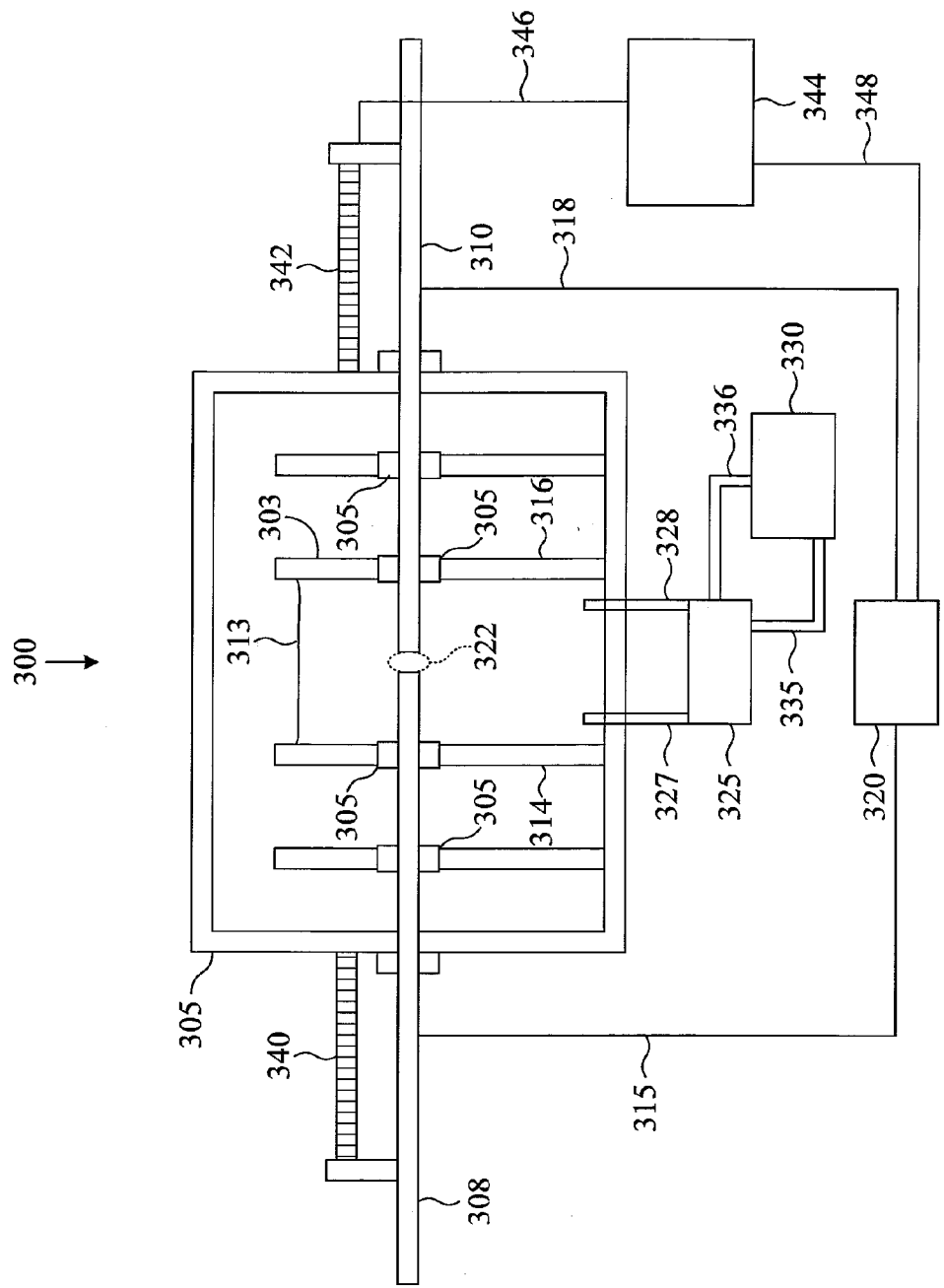
FIG. 6 is a schematic block diagram of an arc in liquid system that can be used to create nano-crystalline dental ceramic powder.

FIG. 6 is a block diagram of an arc-liquid system 300 for producing nanocrystalline dental ceramic powders. Arc cell 305 is chamber within which a reaction may occur between arc-vaporized metal or ceramic atoms and/or ions and a liquid that surrounds the vaporized atoms and/or ions. In the exemplary embodiment shown in FIG. 6, a pair of metal rods 308 and 310 are held with ends that are near each other within a liquid 313. The liquid 313 is contained in a reaction vessel 303 between walls 314 and 316, with the rods 308 and 310 protruding through the walls. The rods 308 and 310 are connected by leads 315 and 318 to a power supply 320, which supplies voltage and current that create an electric arc between the rods, vaporizing a portion of at least one rod and creating a hot plasma 322 formed of the vaporized rod material. The plasma 322 is cooled by the surrounding liquid 313 as the ions of the plasma diffuse into the liquid, which may occur after first transitioning into gas atoms or molecules. The metallic or ceramic ions, atoms or molecules that are produced by the arc discharge may react with the liquid to form dental ceramic crystals. Alternatively, the rods 310 may be made primarily of a desired dental ceramic material that is doped with a metal so that the rods can carry the current needed to form an arc at the gap between the rods, vaporizing the dental ceramic material in the rods, which diffuses into the liquid 313 without reacting with the liquid, to be collected as dental ceramic powder.

A circulation pump 325 is in fluid communication with the vessel 303 via conduits 327 and 328 that protrude through a bottom wall of the chamber 305 and into the vessel, so that the circulation pump 325 circulates the liquid 313 within the vessel. A particle collection system 330 is in fluid communication with the vessel 303, either directly or via the circulation pump 325 as shown, with conduits 335 and 336 transporting liquid 313 into and out of the particle collection system and to collect dental ceramic particles from the liquid. Preferably, the particle collection system 330 can remove the dental ceramic particles from the liquid while the arc cell 305 is producing new dental ceramic particles. The particle collection system 330 may include a centrifuge and/or a filter for separating the particles from the liquid 313 in situ.

In one embodiment, the circulation pump 325 provides liquid 313 containing dental ceramic nanoparticles to the particle collection system 330, which contains a centrifuge that separates the nanoparticles from most of the liquid, forming a nanoparticle slurry. The slurry is then collected and spray-dried to yield a nanoparticle powder. The powder can then be pressed into dental blanks with or without the addition of a binder, which may then be presintered and/or sintered to form dental ceramic prostheses.

In one embodiment, the powder may be made of particles having a mean size in a range between one-half nanometer and thirty nanometers, and a standard deviation from the mean size that is less than twenty percent of the mean size. The powder may contain at least eighty mass percent tetragonal zirconia, and between one-half mass percent and six mass percent yttria. In one embodiment, the powder is made of particles having a maximum size of twenty nanometers.

A motor 342 is attached to rod 308 and a second motor is attached to rod 310 to gradually move the rods toward each other as a part of each rod is ablated by the arc. A computer or controller 344 is connected to the motors 340 and 342 by line 346 and another line not shown, to control the motors. The computer 344 is also connected to power supply 320 to control the voltage and current provided to rods 308 and 310, and the computer may be connected to other elements of the system to facilitate control.

Various materials can be used for liquids 313 and rods 308 and 310 to produce dental ceramic nanoparticles using arc liquid system 300.

For oxide-based dental ceramics, liquids such as water ($H_2O$, preferably deionized), hydrogen peroxide or liquid oxygen may be employed. Further, the liquid 313 may include a dissolved or dispersed gas, such as oxygen. For this category, oxygen gas may be included in water ($H_2O$, preferably deionized), hydrogen peroxide, liquid nitrogen, liquid argon or liquid helium.

For nitride-based dental ceramics, liquids such as liquid nitrogen, liquid ammonia ($NH_3$) or liquid hydrazine ($2NH_2$) may be employed. Also, the liquid 313 may include gas, such as nitrogen, which is dissolved or dispersed in liquid argon or liquid helium.

For carbide-based dental ceramics, liquids such as isopropyl alcohol, methyl alcohol or methyl alcohol may be employed. Also, the liquid 313 may include gas, such as methane or acetylene, which is dissolved or dispersed in liquid argon or water ($H_2O$, preferably deionized).

In addition to the rod and liquid materials listed above, inorganic elemental constituents may be added to the liquid 313. For example, yttrium oxide, iron oxide, chromium oxide, terbium oxide or aluminum oxide can be dissolved or dispersed in the liquid 313. Further, liquid solutions of the following chlorides can be dissolved or dispersed in the liquid 313: yttrium, iron, chromium, terbium or aluminum.

Rods 308 and 310 can be made primarily of zirconium, hafnium, aluminum, tantalum, titanium, niobium or yttrium, for example, as well as oxides, nitrides or carbides of the above, provided the rods are sufficiently conductive to generate an arc between the rods without overheating in other portions of the rods. In addition, minority elements such as iron, terbium, praseodymium, chromium, vanadium, cobalt, nickel, cerium, europium or copper may be included in the rods 308 and 310. It is not necessary for rod 308 to be made of the same material as rod 310, and varying the composition of rod 308 compared to rod 310 provides another technique for creating varied dental ceramic powders. Rods 308 and 310 may have a diameter in a range between about 1 mm and 10 mm, although larger and smaller diameters are possible, and individual rods that are electrically connected via an arc need not have the same size diameters as each other.

Arc liquid system 300 may be particularly suited to producing nanorods, as well as substantially spherical nanocrystals. Particles having a major axis that is no more than five percent larger than their minor axis may be considered to be substantially spherical, whereas particles having a maximum dimension (i.e., length) that is more than four times as large as their minimum dimension may be considered nanorods. Nanorods having a maximum dimension that is more than eight times as large as their minimum dimension may have particular advantages. Dental prostheses formed from dental ceramic powders containing nanorods may have lower birefringence than such prostheses formed from substantially spherical particles, increasing the transmittance. Including a small amount of magnetic material such as iron in the nanorods may allow such nanorods to be aligned by a magnetic field, increasing the density of a powder containing the nanorods and increasing the translucence of a prosthesis formed from the powder. Similarly, the nanorods may be doped with a conductor, allowing alignment of the nanorods with an electric field. In general, dental ceramic nanorods produced by the methods described above may have a maximum dimension in a range between five nanometers and two hundred nanometers, and a respective minimum dimension in a range between less than one nanometer and twelve nanometers. An average maximum dimension for such nanorods may be in a range between five nanometers and one hundred nanometers, and a respective average minimum dimension in a range between one nanometer and ten nanometers. An aspect ratio of at least ten to one for the nanorod dimension may have particular utility.

The conventional sol hydrolysis process method for making powder assumes the particle shape to be spherical based on X-ray diffraction and laser diffraction techniques for determining particle sizes. These methods cannot determine cylindrical or rod shapes, or even whether the particles are spherical. Only direct particle measurement techniques such as scanning electron microscopy (SEM) and transmission electron microscopy (TEM) can determine cylindrical or rod crystallographic texturing, although X-ray diffraction might pick up a small crystallographic texturing intensity. Particle or crystal shape can be directly validated by SEM or TEM at the powder phase, green phase, bisque phase and final sintered phase.

Figure 7A:
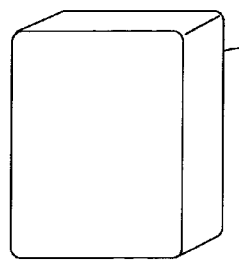
FIG. 7A is a perspective view of a dental blank having six substantially rectangular sides and containing ultrafine dental ceramic powder.
Figure 7B:
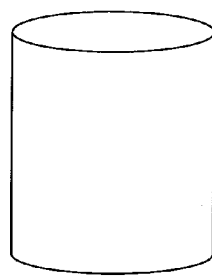
FIG. 7B is a perspective view of a dental blank having a generally cylindrical shape and containing ultrafine dental ceramic powder.
Figure 7C:
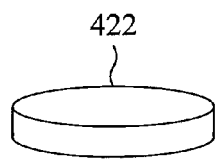
FIG. 7C is a perspective view of a dental blank shaped as a disk and containing ultrafine dental ceramic powder.
Figure 7D:
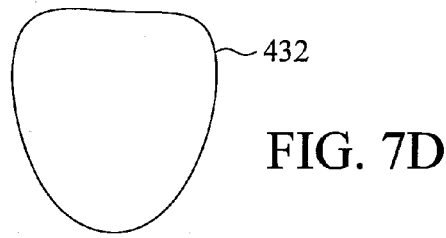
FIG. 7D is a side view of a thin, leaf shaped dental blank containing ultrafine dental ceramic powder.

Ultrafine dental ceramic powder collected by systems 20, 80, 120, 220 or 300 can be formed into intermediate products that are used for dental prostheses, such as dental blanks, shown in FIGS. 8A-8F. Perhaps due to the extremely small average particle size, which may for example have a maximum dimension in a range between one nanometer and five nanometers for substantially spherical particles, or perhaps due to the narrow distribution of particle sizes, which may for example be in a range between less than one nanometer and ten nanometers for substantially spherical particles, the dental ceramic powders may be formed, without any additives or pre-sintering, into a functional dental blank that can be milled and then sintered. For example, all-ceramic, primarily-zirconia blanks can be formed by pressing ultrafine dental ceramic powder into a desired blank size and shape, such as a six sided solid having substantially rectangular sides, sometimes called a die 402, shown in FIG. 7A. FIG. 7B shows a generally cylindrical, binder-free, primarily-zirconia dental blank 412 formed of packed, ultrafine dental ceramic powder, while FIG. 7C shows a disk-like blank 422 made of similar materials. FIG. 7D shows a thin, translucent, binder-free, primarily-zirconia dental veneer 432 formed of pressed, ultrafine dental ceramic powder, which may be a scaled replica of a sintered transparent veneer.

Figure 7E:
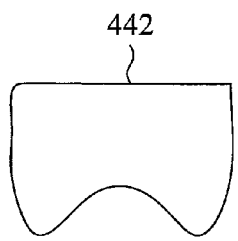
FIG. 7E is a cross-section of a near-net blank formed in the shape of a crown for an adult human molar.
Figure 7F:
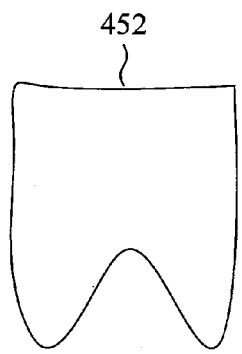
FIG. 7F is a cross-section of a near-net blank formed in the shape of an adult human molar.

Alternatively, the ultrafine dental ceramic powders may be pressed into a "near net shape," which conserves the powder lost during milling by forming blanks that are shaped similarly to but larger than the particular tooth or teeth to be replaced. FIG. 7E shows a cross-section of a near-net blank 442 formed in the shape of a crown for an adult human molar, whereas FIG. 7F shows a cross-section of a near-net blank 452 formed in the shape of an adult human molar. Near-net blanks of ultrafine dental ceramic powders can be formed for various categories and sizes of human teeth, such as incisors, canines, premolars and molars, as well as for crowns, veneers or bridges of such different teeth.

Along with pressing, the dental ceramic powder may be vibrated at a high frequency and low amplitude to condense the powder into a solid form, with care taken not to transform tetragonal zirconia to monoclinic zirconia, and nanorod particles may be subjected to electric or magnetic fields, as mentioned above. As an example, tetragonal-zirconia/yttria powder formed as described above can be used to create all ceramic blanks that have a density of greater than sixty percent of theoretical density despite being made entirely of particles that are less than ten nanometers each, in contrast to conventional wisdom that green state density is higher with large agglomerated particles that contain no pores, interspersed with smaller particles that fill pores between the large particles. Dense, purely ceramic blanks made of packed, ultrafine tetragonal-zirconia/yttria powder appear to reflect green light. As described below, milling and sintering of such purely ceramic blanks made of packed, ultrafine tetragonal-zirconia/yttria powder yields dental ceramic prostheses with superlative attributes, such as flexural strength exceeding 800 mega-Pascals and having a translucence and color very similar to the outer layers of natural teeth. Because the pressure from compacting can transform some of the tetragonal zirconia to monoclinic zirconia, reducing the compaction pressure reduces the tetragonal to monoclinic transformation. However, reduced compaction pressure increases the porosity which reduces the strength. We have found that there is an optimal strength by balancing these two competing affects.

Alternatively, the ultrafine dental ceramic powders may be mixed with a binder and then formed into dental blanks, for example by pressing or injection molding, the blanks then pre-sintered into a bisque state prior to shaping by milling and then sintering. For this situation, FIGS. 8A-8F can represent bisque-state blanks formed by heating blank-shaped mixtures of ultrafine dental ceramic powders and binder to a temperature of between 200° C. and 1700° 0 for a period of between 30 minutes and 48 hours, or until the binder has been essentially completely removed. Alternatively, FIGS. 8A-8F can represent bisque-state blanks formed by heating blank-shaped, pure ultrafine dental ceramic powders to a temperature of between 200° C. and 1700° C. for a period of between 30 minutes and 48 hours. Pre-sintering blank-shaped, pure, ultrafine dental ceramic powders yields blanks that are strong yet easily and exactingly milled with common milling tools and equipment. Alternatively, ultrafine dental ceramic powders mixed with binder can be painted on dental prostheses such as dentures or crowns and sintered to form a hard, translucent veneer.

After milling of the blanks into a desired shape, the shaped intermediate products can be sintered. A shaped intermediate product may be an oversized replica of a final dental product such as a prosthetic tooth, the oversize calculated based on the predicted amount of shrinkage due to sintering. The proportionately greater surface area of the green-state, packed, ultrafine powder intermediate product, or of the bisque-state intermediate product created from the ultrafine powder, allows the intermediate products to be sintered at a lower temperature and/or for a shorter time than is conventional. For example, either the green-state or bisque-state intermediate product made from ultrafine primarily zirconia powder can be sintered at a temperature of between 400° C. and 1600° C. for a period of between 30 minutes and 48 hours, or at a temperature of between 200° C. and 1700° C. for a period of between 30 minutes and 48 hours.

Figure 8:
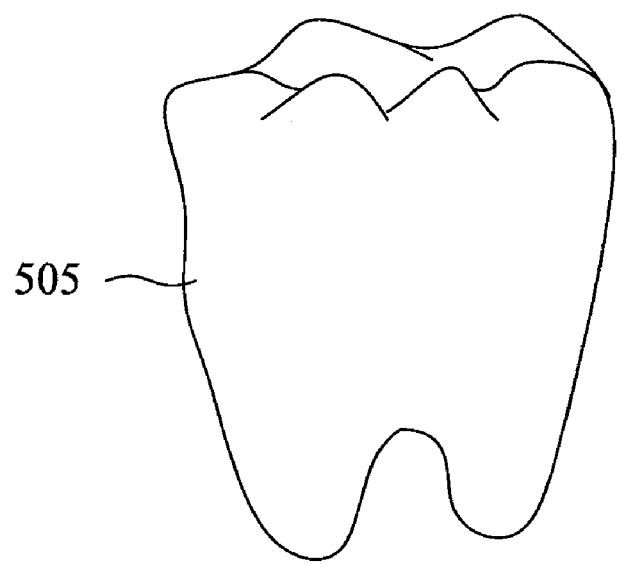
FIG. 8 is a perspective view of a prosthetic tooth made of ultrafine dental ceramic crystals.

FIG. 8 shows a dental device 505, which in this embodiment is a prosthetic third molar tooth. Dental device 505 may include in one embodiment at least eighty nine percent (mol %) dental ceramic molecules in the form of substantially spherical crystals having a maximum dimension that is less than 40 nm. Alternatively, dental device 505 may be formed from nanorods and may include in one embodiment at least eighty nine percent (mol %) dental ceramic molecules in the form of anisotropic crystals having dimensions with an aspect ratio of at least four to one. The anisotropic crystals may have having an average maximum dimension that is less than 200 nm. The dental prosthesis 505 has a flexural strength that is between six hundred mega-Pascals and two thousand mega-Pascals, wherein a one millimeter thickness of the body has an optical transmittance of between twenty percent and ninety-five percent for a wavelength of light that is between four hundred nanometers and seven hundred nanometers. The dental ceramic crystals may be primarily zirconium oxide, aluminum oxide, hafnium oxide, niobium oxide or yttrium oxide.

In one exemplary embodiment, the dental ceramic crystals are primarily tetragonal zirconia polycrystal (TZP), which is a solid blend of zirconium and about three atomic percent yttria. The mean size of the crystals may be less than twenty four nanometers. Other exemplary compositions of dental ceramic molecules that can form dental device 505 include the following: composition 1: zirconia (99.5%-90%) and yttria (0.5%-10%), at. %; composition 2: zirconia(99.49%-90%), yttria(0.5%-9%) and alumina (0.001%-1%), at. %; composition 3: zirconia(99.99%-90%) and alumina (0.001%-10%), at. %; composition 4: zirconia(99.49%-89%), yttria(0.5%-9%), alumina (0.001%-1%) and iron oxide (0.005%-1.0%), at. %; composition 5: zirconia(99.49%-89%), yttria(0.5%-9%), alumina (0.001%-1%) and terbium oxide (0.005%-1.0%), at. %.

Figure 9:
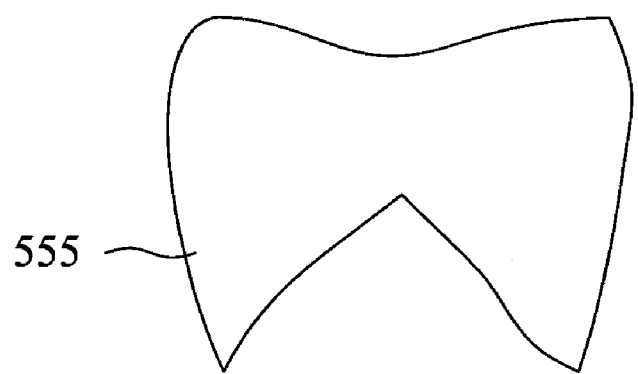
FIG. 9 is a cross-sectional view of a prosthetic tooth crown made of ultrafine dental ceramic crystals.

FIG. 9 shows cross-section of a dental device 555, which in this embodiment is a crown for a molar tooth. Dental device 555 was formed from dental ceramic powder in which substantially all dental ceramic particles had a maximum dimension of less than ten nanometers prior to sintering, as described above. After sintering, dental device 555 is translucent and essentially free of pores, having an average crystal size of less than forty nanometers. Dental device 555 has a flexural strength between eight hundred mega-Pascals and two thousand mega-Pascals, and has an optical transmittance for a one millimeter thickness of between thirty-five percent and ninety-five percent for a wavelength of light that is between four hundred nanometers and seven hundred nanometers.

Alternatively, dental device 555 may be formed from dental ceramic powder in which the dental ceramic particles are nanorods with a diameter of less than ten nanometers prior to sintering, as described above. After sintering, dental device 555 is translucent and may have, for a nanorod based material, an average crystal aspect ratio of at least eight to one.

Dental prosthetic devices such as devices 505 and 555 can have a density that is greater than ninety five percent of the theoretical maximum density when sintered at a relatively low sintering temperature of between 800° C. and 1000° C. That percentage rises to greater than and ninety eight percent when sintered above 1000° C., and greater than ninety nine and one-half percent when sintered at or above 1100° C. A density that is greater than ninety nine and one-half percent of theoretical may be considered to be essentially pore free. Sintering in a vacuum can increase the density further for each of the above temperature ranges.

The foregoing description has been presented for the purposes of illustration and example. It is not intended to be exhaustive or to limit the invention to the precise form disclosed. It is intended that the scope of the invention be limited not by this description including these drawings, but rather by the claims appended hereto. Any advantages and benefits described may not apply to all embodiments of the invention.

The invention claimed is:

1. A dental device comprising:
    a solid body containing at least forty mass percent tetragonal zirconia in the form of crystals having a length and a width such that the length is at least twice as large as the width, the body shaped in the form of a dental prosthesis and characterized by having a flexural strength between eight hundred mega-Pascals and two thousand mega-Pascals, and having an optical transmittance for a one millimeter thickness of between thirty-five percent and ninety-five percent for a wavelength of light that is between four hundred nanometers and seven hundred nanometers.

2. The device of claim 1, wherein the body contains at least eighty-nine atomic percent zirconia and between one-half atomic percent and six atomic percent yttria.

3. The device of claim 1, wherein the length is at least four times as large as the width.

4. The device of claim 1, wherein the length is at least eight times as large as the width.

5. The device of claim 1, wherein the crystals are formed from tetragonal zirconium oxide particles made by vaporization of zirconium or zirconium oxide.

6. A dental device comprising:
   a bisque-state solid body containing at least eighty mass percent tetragonal zirconium oxide crystals having a mean size of between one nanometer and fifty nanometers, and a standard deviation from the mean size that is less than twenty percent of the mean size, the body shaped in the form of a dental blank and having a density that is between fifty percent and ninety percent of a theoretical maximum density of the body.

7. The device of claim 6, wherein the solid body contains between one-half mass percent and six mass percent yttria.

8. The device of claim 6, wherein the crystals have a length to width aspect ratio of at least two to one.

9. The device of claim 6, wherein the crystals have a length to width aspect ratio of at least four to one.

10. A dental device comprising:
    a bisque-state solid body containing at least eighty mass percent tetragonal zirconium oxide crystals having a length to width aspect ratio of at least two to one, the body shaped in the form of a dental blank and having a density that is between fifty percent and ninety percent of a theoretical maximum density of the body.

11. The device of claim 10, wherein at least thirty mass percent of the crystals have a length to width aspect ratio of at least four to one.

* * * * *